United States Patent [19]
Gaultney et al.

[11] Patent Number: 5,044,756
[45] Date of Patent: Sep. 3, 1991

[54] REAL-TIME SOIL ORGANIC MATTER SENSOR

[75] Inventors: Lawrence D. Gaultney; George E. Van Scoyoc; Darrell G. Schulze, all of West Lafayette, Ind.; Jason L. Shonk, Woodridge, Ill.

[73] Assignee: Purdue Research Foundation, West Lafayette, Ind.

[21] Appl. No.: 325,698

[22] Filed: Mar. 13, 1989

[51] Int. Cl.$^5$ .................. G01N 21/49; G01N 21/84; G01N 33/24

[52] U.S. Cl. .................................. 356/446; 356/72; 356/402

[58] Field of Search .................. 356/72, 445–448, 356/402

[56] References Cited

U.S. PATENT DOCUMENTS 4,266,878  5/1981  Auer ................................. 356/419

OTHER PUBLICATIONS

"Undercover Light 'Reads' Soil Organic Level", *Successful Farming*, Planning Issue, p. 56-L (Nov., 1987).
G. Mangold, "New Tool Prescribes Precise Nitrogen Needs", *Soybean Digest*, p. 16b–16c (Feb. 1988).
J. L. Shonk & L. D. Gaultney, "Spectroscopic Sensing for the Determination of Organic Matter Content", Paper #88-2142, presented at the International Summer Meeting of the American Society of Agricultural Engineers, Jun. 26–29, 1988.
R. N. Fernandez, D. G. Schultze, D. L. Coffin, and G. E. Scoyoc, entitled "Color, Organic Matter, and Pesticide Adsorption Relationships in a Soil Landscape", (Jul.–Aug. 1988), *Soil Science of America Journal*.
P. Krishman, B. J. Bulter, J. Hummel, "Close-Range Sensing of Soil Organic Matter", *Trans. Amer. Soc. Agric. Eng.*, 24:306–311 (1981).
J. L. Ruckman, J. W. Hummel, and B. J. Butler, "Improved Soil Organic Matter Sensor With Microprocessor Control", Paper No. 81-1012 presented before the American Society of Agricultural Engineers, St. Joseph Michigan (1981).
M. J. Pitts, J. W. Hummel, and B. J. Butler, "Sensors Utilizing Light Reflection to Measure Soil Organic Matter", Paper No. 83-1011 presented before the American Society of Agricultural Engineers, Bozeman, Montana (1983).
C. L. Griffis, "Electronic Sensing of Soil Organic Matter", *Trans. Amer. Soc. Agric. Eng.*, 28:703–705 (1985).
R. M. Hoffer, "Biological and Physical Consideratiions in Applying Computer-Aided Analysis Techniques to Remote Sensor Data", *Remote Sensing: The Quantitative Approach*, Chapt. 5 (1978).
J. A. Shields, E. A. Paul, R. J. St. Arnaud and W. K. Head, "Spectrophotometric Measurement of Soil Color and Its Relationship to Moisture and Organic Matter", *Can. J. Soil Sci.*, vol. 48, pp. 271–280 (1968).
S. A. Bowers and R. J. Hanks, "Reflection of Radiant Energy from Soils", *Soil Science*, vol. 100, No. 2, pp. 130–138 (1965).

*Primary Examiner*—Vincent P. McGraw
*Attorney, Agent, or Firm*—Barnes & Thornburg

[57] ABSTRACT

An apparatus for attachment to a vehicle for sensing the organic matter content of soil at a soil scene as it is moved through the soil by the vehicle has a probe including a housing, a light source and a light sensor. The light sensor senses the light reflected from the soil scene and produces an output signal which is related to the organic matter content of the soil at the soil scene. The housing is attached to the vehicle so that as it is moved through the soil the soil scene that is observed by the light sensor is beneath the surface of the surrounding soil and the housing shields the soil scene from ambient light. The apparatus also includes a processor which processes the signal from the light sensor using data predetermined from a particular landscape which includes the soil to be sensed.

18 Claims, 5 Drawing Sheets

REAL-TIME SOIL ORGANIC MATTER SENSOR

This invention relates to soil content sensors, and more particularly, to an apparatus for sensing the organic matter content of soil.

The organic matter content of a soil is a significant variable in modern soil management and is included in many relationships involving the soil solum. A soil's adsorption of pesticides, its water holding capacity, and its yield potential are often related to its organic matter content.

Conventional agricultural equipment is designed to apply chemicals and plant crops at uniform rates within a field, regardless of changes in soil type or organic matter content. This can result in an overapplication of chemicals in some areas of the field, an underapplication in other areas, overplanting in some areas and underplanting in others. It would therefore be desirable to provide a prescription application system which would rapidly and accurately adjust chemical and seeding rates by sensing variations in soil type and organic matter as equipment traverses a field. There is thus a need for an apparatus that will sense the organic content of soil as chemicals are being applied or crops planted so that the application of the chemicals or the seeding can be adjusted based upon the sensed organic matter content of the particular area of the field to be treated or planted.

In the past decade, there has been interest in developing agricultural equipment capable of sensing soil organic matter content and adjusting the corresponding herbicide application rate as the equipment moves across the field. [P. Krishnan, B. J. Butler & J. Hummel, "Close-range Sensing of Soil Organic Matter," *Trans. Amer. Soc. Agric. Eng.*, 24:306-311 (1981); J. L. Ruckman, J. W. Hummel & B. J. Butler, "Improved Soil Organic Matter Sensor with Microprocessor Control," Paper No. 81-1012 presented before the American Society of Agricultural Engineers, St. Joseph, Michigan (1981); M. J. Pitts, J. W. Hummel and B. J. Butler, "Sensors Utilizing Light Reflection to Measure Soil Organic Matter," Paper No. 83-1011 presented before the American Society of Agricultural Engineers, Bozeman, Montana (1983); C. L. Griffis, "Electronic Sensing of Soil Organic Matter," *Trans. Amer. Soc. Agric. Eng.*, 28:703-705 (1985)] Such sensing systems require knowledge of the mathematical relationship between organic matter content and soil color.

In general, progress in developing such sensor systems has proven to be unsatisfactory because the developers have attempted to develop universal relationships between organic matter content and sensor output. The problem with this approach is that it is known that different soil associations can have different relationships between organic matter content and soil color.

Another problem faced in developing an accurate real-time soil organic matter sensor is that the scene, i.e., particular area of the soil that is being observed by the sensor, must have a generally uniform surface. These sensors typically work by reflecting light off the scene. If the surface of the scene is not uniform, the reflectance will vary in response to surface roughness changes yielding erroneous results. Variations in the surface of the scene can be caused by differences in soil texture, size of the soil aggregates, moisture content, etc. Ambient light can also adversely affect the accuracy of such sensors by introducing a second, variable source of light which is also reflected from the scene and picked up by the sensor.

Recently, an article about this invention described certain concepts used in this invention to address some of the above described problems. ["Undercover Light 'Reads' Soil Organic Level," *Successful Farming*, Planning Issue, 56-L (Nov., 1987)] This article mentioned the concept of using light emitting diodes to reflect light off the soil to be measured and then measuring the reflected light which correlates with the organic matter content in the soil. The concept of mounting the light source and sensor on a shank to hold them below the surface of the soil so that the readings were taken in moist soil was also mentioned in this article.

It is an object of this invention to provide an apparatus for sensing the organic matter content of soil on a real-time basis.

It is also an object of this invention to provide a soil sensor that reduces problems caused by variations in soil moisture and surface roughness and problems caused by ambient light.

An apparatus, constructed according to this invention, for sensing the organic matter content of soil has a probe including a housing, a light source and a light sensor. The apparatus is attached to a vehicle which moves the probe through the soil. The light source and light sensor are mounted in the housing so that light from the light source will be directed onto a soil scene and such that the light sensor will sense light from the light source that is reflected from the soil scene. The housing also shields the soil scene, light source and light sensor from ambient light. Further, the housing is attached to the vehicle so that as it is moved through the soil the soil scene against which light from the light source is directed is below the surface of the surrounding soil. The light reflected from the soil scene that is sensed by the light sensor is indicative of the organic matter content of the soil at the soil scene.

The apparatus also preferably includes a member that prepares the surface of the soil scene immediately before it is observed by the sensor to provide a generally uniform surface, i.e., generally flat and smooth. Further, the light source preferably comprises red light-emitting diodes that are arranged circularly about the light sensor which is preferably a photodiode.

The apparatus also preferably includes a processor that processes the light sensed by the light sensor to determine the organic matter content of the soil at the soil scene. The processor preferably has data reflecting an experimentally determined characterization of the soil in the local geographic area where the soil being sensed is located. Preferably, this data comprises a mathematical equation for different classes of soils, e.g., a linear regression equation for soils having a low sand content and a curvilinear regression equation for soils with a relatively higher sand content. Further, each such equation has parameters which are determined from the particular landscape where the apparatus is used. The processor uses the appropriate mathematical equation to solve for the organic matter content of the soil using the sensed reflected light as an input to the equation.

Additional features and advantages of the invention will become apparent to those skilled in the art upon consideration of the following detailed description of a preferred embodiment, exemplifying the best mode of carrying out the invention as presently perceived. The detailed description particularly refers to the accompanying figures in which.

Figure 1:
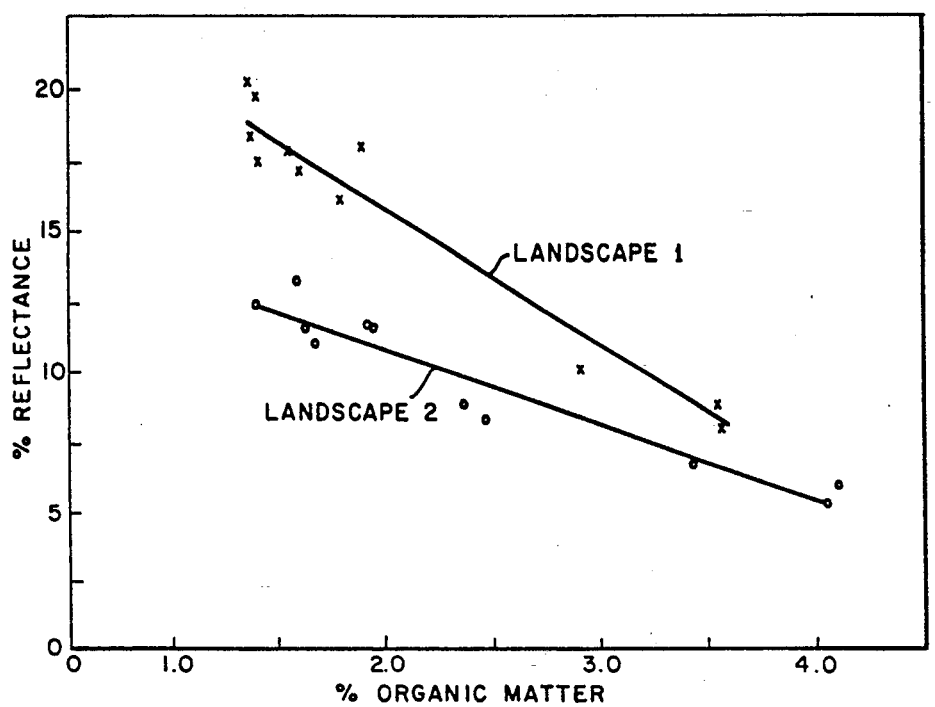
FIG. 1 is a plot showing the relationship between reflectance and organic matter content in medium and fine textured soils.

Chemical and physical properties vary from soil to soil and affect the reflectance and absorption characteristics of each soil. Color is an obvious soil property and can be used as an indirect measure of other soil characteristics.

Conceptually, a system for close range remote sensing of soil color, including the soil itself, can be characterized as having four basic components—an illumination device, a scene, a sensor, and an algorithm processor. The illumination device is illustratively an active light source that can be concentrated on the scene. The scene is the portion of the soil surface observed by the sensor. The desired information is contained in the spectral variations of the electromagnetic energy emanating from the scene. The sensor collects the energy and measures its features. The processor will typically implement a deterministic algorithm which will make an appropriate estimation based on feature measurements provided by the output from the sensor. As will be discussed in more detail later, the apparatus of this invention senses the magnitude of light, illustratively provided from a monochromatic source, that is reflected from the scene and determines the organic matter content based on the magnitude of the reflected light.

Soil is a heterogeneous substance and thus has a variety of different factors that affect reflectance. The reflectance of electromagnetic energy and the factors that attenuate the amplitude of the electromagnetic energy reflected from a soil surface must be considered in an appropriate sensor design. The factors affecting soil reflectance are texture, moisture content, surface roughness, iron oxide content, and organic matter content. Because of this multivariant relationship, it is important to understand how these five variables affect reflectance.

Soil texture is the classification of soil by the size distribution of < 2 mm mineral particles. The relative percentages of sand, silt and clay affect light reflectance because of its relationship with aggregate diameter and moisture content. It is known that reflectance increases exponentially when particle size changes from 2500 $\mu$m to 25 $\mu$m. [S. A. Bowers and R. J. Hanks, "Reflection of Radiant Energy from Soils," *Soil Science*, 100(2):130–138 (1965)] Large particles reflect less energy due to larger void spaces between particles which cause additional scattering and absorption of light. Texture also affects reflectance because different textures have different moisture holding capacities. The effect of soil texture can be controlled by constraining the experimental inference area so that textural changes are minimized. For example, a state such as Indiana could be divided into soil regions based on similar soil textures instead of inferring across the entire state.

Water absorbs electromagnetic energy mainly in the infrared region. Water absorption bands found at 1400 and 1900 nm represent overtones of the fundamental frequencies (2660, 2730, and 6270 nm) at which water molecules vibrate. [R. M. Hoffer, "Biological and Physical Considerations in Applying Computer Aided r Analysis Techniques to Remote Sensor Data," *Remote Sensing: The Quantitative Approach*, P. H. Swain and S. M. Davis (ed) (1978)]. Water alters soil reflectance in the visible wavelengths by reducing the scattering of light from soil particles. It is known that the amount of attenuation from moisture is not linear. For example, one study found that the amount of light reflected from a soil decreased as moisture was added but that in a range of 20% to 40% moisture content, reflectance did not significantly change [J. A. Shields, E. A. Paul, R. J. St. Arnaud and W. K. Head, "Spectrophotometric Measurement of Soil Color and its Relationship to Moisture and Organic Matter," *Can. J. Soil Sci.*, 48:271–280 (1968)]

Variations in moisture content are much more severe at surface level than beneath the soil surface. At the surface level, moisture can vary exceedingly due to differential drying of the surface, residue cover, and changes in topography. Beneath the soil surface, however, moisture content is more uniform and at a level where a slight variance in moisture content might not significantly affect reflectance.

A major variable affecting soil reflectance is the surface roughness. The energy reflected from a soil surface is decreased by increased surface roughness. Surface roughness tends to be more of a problem at closer ranges due to a smaller sampling area. The rough surface diffuses light over a larger scene than is normally viewed by the sensor.

Surface roughness is predominately determined by soil tillage practices. A minimum tillage practice tends to create a rougher surface than conventional tillage practice where larger soil aggregates are reduced in size by increased tillage processes. Thus, it is important to provide for some minimum amount of soil conditioning to produce a uniform, constant surface when attempting to determine the organic matter content of soil by light reflectance, regardless of any previous tillage of the soil. Agricultural soils also contain varying amounts of surface residue. It is important that this surface residue be removed from the scene to assure that only soil is being observed by the sensor.

It is also known that iron oxides can have a significant influence on the spectral reflectance of the soil. [R. M. Hoffer, "Biological and Physical Considerations in Applying Computer Aided Analysis Techniques to Remote Sensor Data," *Remote Sensing: The Quantitative Approach*, P. H. Swain and S. M. Davis (ed) (1978); E. R. Stoner and M. F. Baumgardner, "Physiochemical, Site, and Bidirectional Reflectance Factor Characteristics of Uniformly Moist Soil," Laboratory for the Application of Remote Sensing, Technical Report 111679, Purdue University, West Lafayette, Ind. (1980). For example, in Indiana, the dominant iron oxides are goethite and hematite. They absorb energy in the majority of visible and infrared wavelengths except for some areas in the yellow and red regions. Therefore, it would be advantageous to use an illumination source that would emit energy in either the red or yellow regions to constrain the variables absorbing light. It has been found that organic matter contents greater than about 2 percent tend to mask the effect of iron oxides. M. F. Baumgardner, S. J. Kristof, C. J. Johannssen and A. L. Zachary, "The Effects of Organic Matter on Multispectral Properties of Soils," *Proc. Indiana Acad. Sci.,* 79:413–422 (1970)]However, in eroded circumstances, the soil surface is lost and iron oxides present in the subsurface horizons become a large factor in soil reflectance.

Heretofore, previous studies have typically used a white light source as the artificial illumination device and optical filters to achieve a very narrow band of light energy. Employing a concentrated narrow band approach, similar to that disclosed in C. L. Griffis, "Electronic Sensing of Soil Organic Matter," *Trans. of the ASAE,* 28:703–705 (1985), would eliminate the need for filtering. Applicants have found that red light emitting diodes (LEDs) can be used advantageously because they emit light having a wavelength where effects from iron oxides are hypothesized to be less, relative to other reflective wavelengths.

In a study conducted in the laboratory using a prototype probe constructed according to the principles of this invention, applicants found that soils having medium to fine textures exhibit a linear relationship between light reflectance and organic matter content as shown in FIG. 1. Since the quantity of light reflected is dependent on the organic matter content, a linear regression model is used to determine organic matter content from the light reflected for soils having medium to fine textures. This model is:

$$R_i = B_0 + B_1 X_i + \epsilon_i \quad [1]$$

where:
$R_i$ is the light reflectance measured in millivolts of the $i^{th}$ sample;
$X_i$ is the percent organic matter content of the $i^{th}$ sample;
$B_0$ & $B_1$ are parameters; and
$\epsilon_i$ is a random error term NID (0, $\sigma^2$).
Solving for $X_i$ yields:

$$X_i = [R_i - B_0] * B_1^{-1} \quad [2]$$

In most cases, $\epsilon_i$ will be zero since the light reflectance values, R, will be distributed evenly about zero, i.e., the line predicted by equation [1] with $\epsilon_i$ set to zero.

Figure 2:
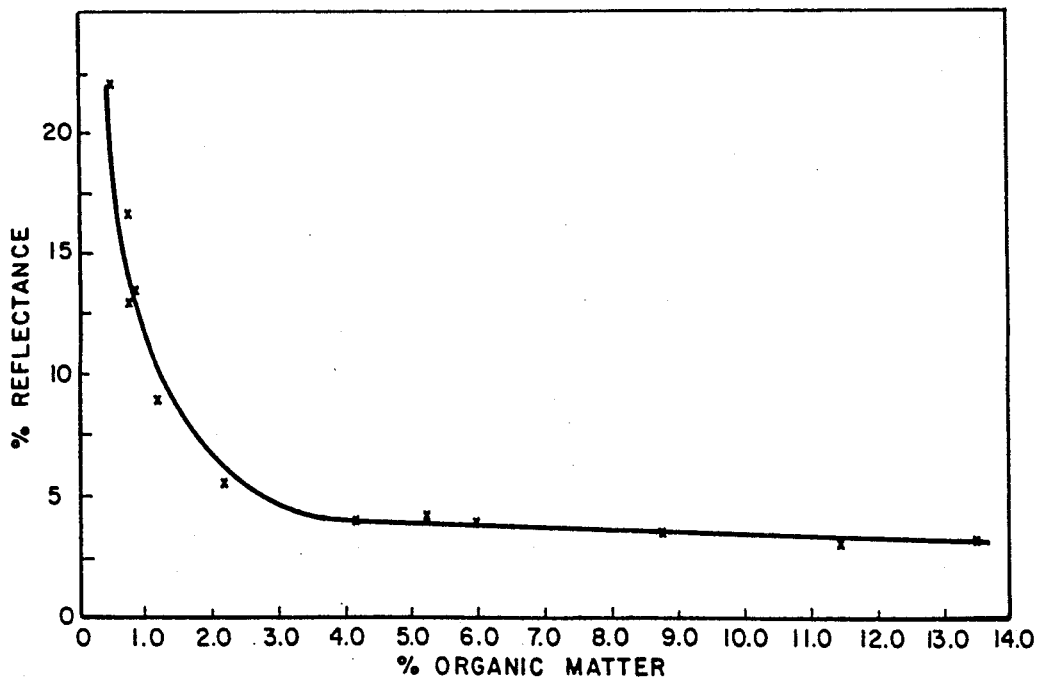
FIG. 2 is a plot showing the relationship between reflectance and organic matter content in a soil having a relatively higher sand content.

Applicants also found in their study that soils having a high percentage of sand frequently exhibit a curvilinear relationship as shown in FIG. 2. However, this relationship was found to be very predictable. Transforming the independent variable (organic matter content) into its inverse allows the resulting model to better fit the reflected light curve.

$$R_i = B_0 + B_1 X_i^{-1} + \epsilon_i \quad [3]$$

Solving for $X_i$ yields:

$$X_i = B_1 * [R_i - B_0]^{-1} \quad [4]$$

Again, $\epsilon_i$ will usually be zero for the same reason as discussed above.

In their study, applicants also found that when the organic matter content increased above 6% it became increasingly difficult to determine the organic matter content using reflectance data. However, in most landscapes, the quantity of organic matter rarely exceeds 5–6%. Further, it is probably not economical to use a pre-emergence herbicide in soils having an organic matter content greater than 6% so this is not likely to be a major limitation on the use of this invention.

Figure 3:
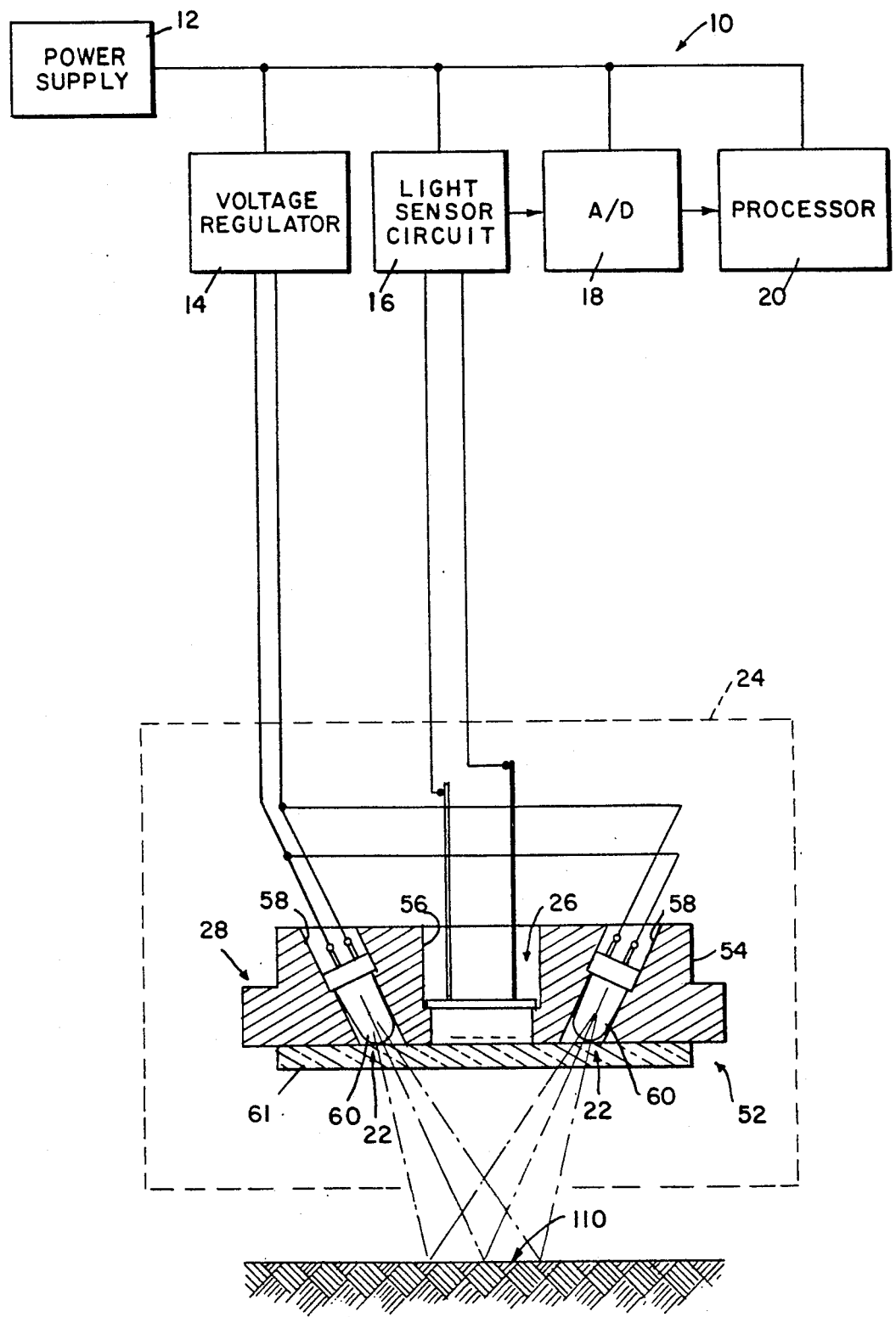
FIG. 3 is a partially block diagram and partially perspective view of an apparatus for determining the organic matter content of soil constructed according to this invention.
Figure 4:
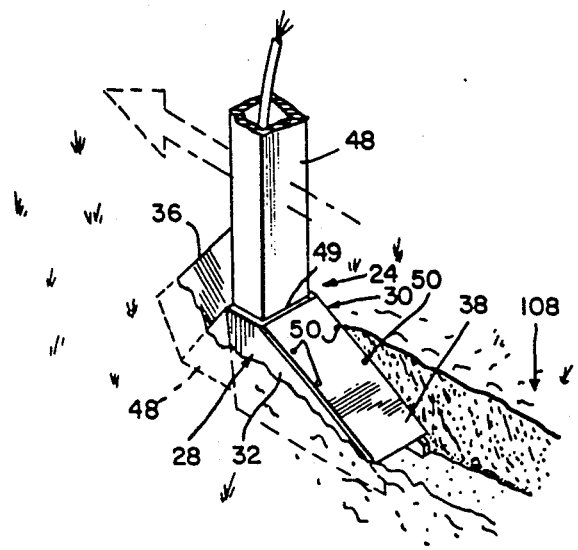
FIG. 4 is a perspective view of a probe of the apparatus of FIG. 3.
Figure 5:
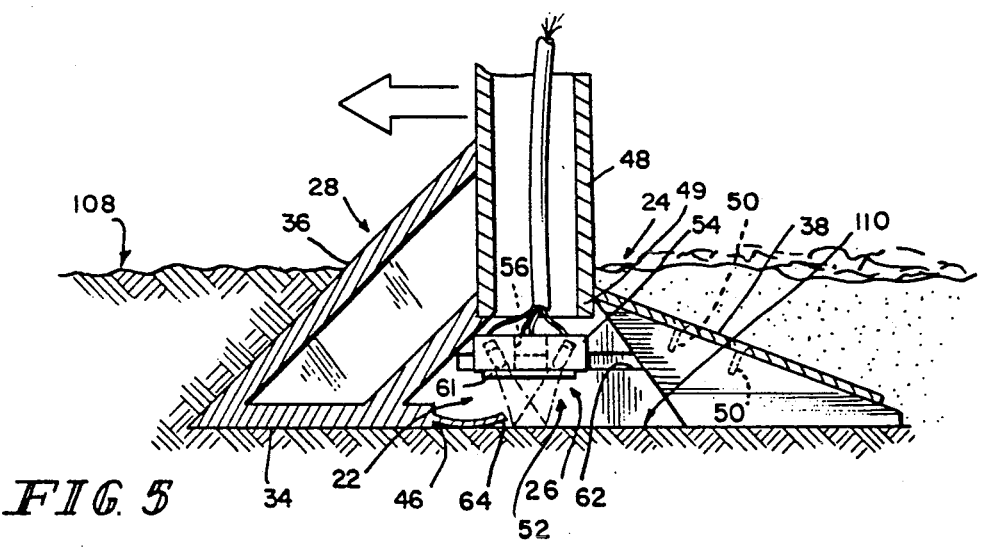
FIG. 5 is a transverse view and elevation of the probe of FIG. 4.
Figure 6:
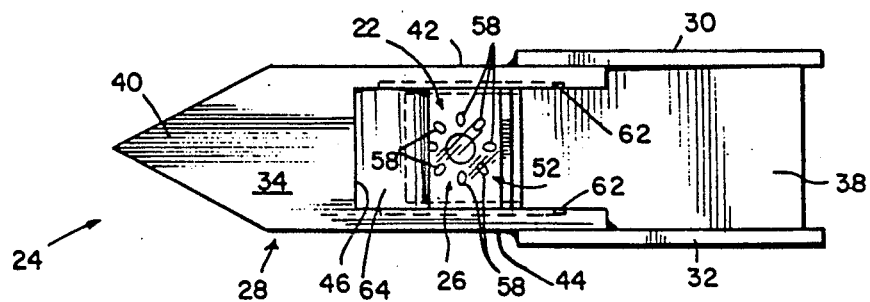
FIG. 6 is a bottom view of the probe of FIG. 4.

Referring to FIG. 3, an apparatus 10 for sensing the organic matter content of soil on a real-time basis has a power supply 12 for providing power to the electronic components of apparatus 10. Power supply 12 is coupled to a voltage regulator 14, a light sensor circuit 16, an analog-to-digital converter 18, and to a processor 20. Voltage regulator 14 is coupled to a light source 22 of a probe 24. Probe 24 also includes a light sensor 26 and a housing 28 in which light source 22 and light sensor 26 are mounted. As will be described in more detail later, light source 22 comprises a plurality of light emitting diodes (LEDs) arranged circularly around light sensor 26 which illustratively comprises a photodiode. Light sensor 26 is coupled to light sensor circuit 16. An output of light sensor circuit 16 is coupled to an input of analog-to-digital converter 18. An output of analog-to-digital converter 18 is coupled to processor 20.

Referring to FIGS. 3–6, probe 24 is described in greater detail. Housing 28 of probe 24 is a shoe-like structure having opposed truncated triangular sidewalls 30, 32. Housing 28 also includes a bottom 34, a front plate 36 and a back cover 38. Bottom 34 has a v-shaped nose 40 and opposed sidewalls 42, 44 which extend rearwardly from a rear edge 46 of bottom 34. Sidewalls 42, 44 of bottom 34 are affixed, such as by welding, to sidewalls 30, 32 at front edges of sidewalls 30, 32. Front plate 36 is a generally v-shaped plate that extends upwardly and rearwardly from nose 40 of bottom 34 to an arm 48. Front plate 36 is affixed, such as by welding, to bottom 34, to sidewalls 30, 32 along front edges thereof, and to the front of arm 48. Back cover 38 is affixed, such as by screws 50, to sidewalls 30, 32 along upper rear edges thereof. Back plate 38 extends from a rear edge of arm 48 to the rearmost edges of sidewalls 30, 32 and thus covers the rear portion of housing 28.

Probe 24 also includes means 52 for mounting light source 22 and light sensor 26 in housing 28. Mounting means 52 comprises a block 54 having a hole 56 extending vertically therethrough and a plurality of angled holes 58 extending therethrough arranged circularly about hole 56. Mounting means 52 also includes slots 62 extending horizontally in sidewalls 42, 44 of bottom 34 which receive outer edges of block 54 which is then secured in slots 62 in a conventional fashion. LEDs 60 comprise light source 22. There are illustratively eight red LEDs 60 having a combined luminous flux of 11.43 lumens on 68.52 mm$^2$. The photodiode that is light sensor 26 is selected to have optimum sensitivity to red light. Slots 62 are positioned within side walls 42, 44 of bottom 34 so that light sensor 26 and light source 22 are held an optimal distance above a soil scene 110, illustratively, one inch. Holes 58 are positioned in block 54 so that an intense beam of light from LEDs 60 is focused on a plane one inch below the diodes. The photodiode that is light sensor 26 is mounted within hole 56 so that it is positioned directly above this focal point. A sheet 61 of transparent material such as glass or Plexiglass is affixed to the bottom of block 54 to shield light source 22 and light sensor 22 from dirt.

Probe 24 also includes means for conditioning the soil surface of the soil scene 110 immediately before it is observed by light sensor 26. The soil surface conditioning means comprises an arcuate flange 64 that is curved about its longitudinal axis and extends transversely across the bottom of housing 28. Arcuate flange 64 is mounted to bottom plate 34 at the rear edge 46 thereof and extends rearwardly therefrom and contacts the soil with a convex surface.

Arm 48 is used to attach probe 24 to a vehicle (not shown) such as a farm tractor. Arm 48 has a distal end 49 that is affixed to the top of housing 28 such as by welding to front plate 36 and to sidewalls 30, 32.

Figure 7:
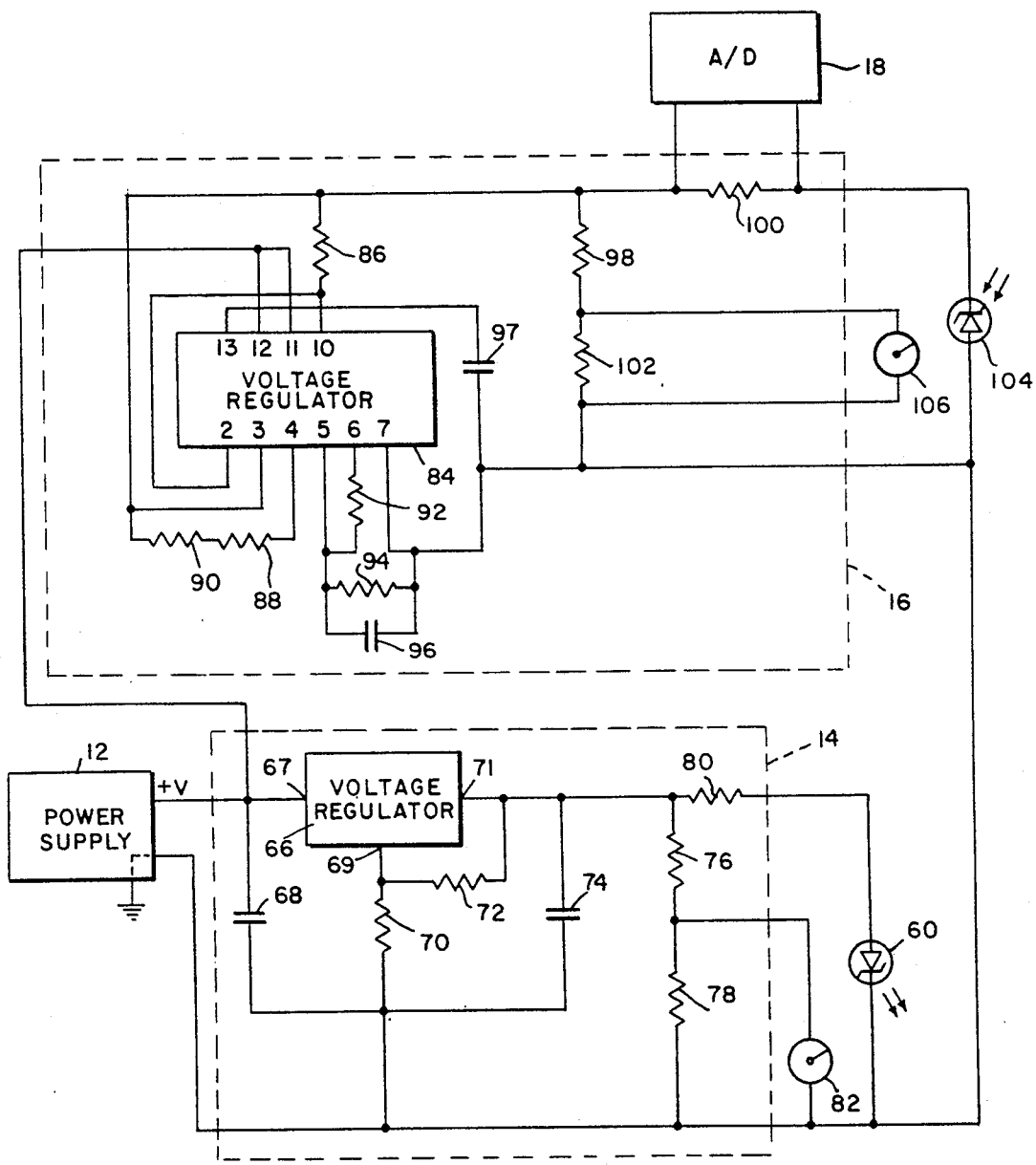
FIG. 7 is a schematic of a circuit for a light source and light sensor of the probe of this invention.

FIG. 7 is a schematic of a circuit for voltage regulator 14 and light sensor circuit 16 of FIG. 1. Voltage regulator 14 includes a voltage regulator chip 55 that has a voltage input 67 coupled to a +V output, illustratively +12 VDC, of power supply 12 and through a 0.1 μf capacitor 68 to a common terminal of power supply 12. An adjust input 69 of voltage regulator chip 66 is coupled through a 2.2K resistor 70 to the common terminal of power supply 12. A voltage output 71 of voltage regulator chip 66 is coupled through a 390 ohm resistor 72 to the adjust input 69 of voltage regulator chip 66, through a 1 μf capacitor 74 to the common terminal of power supply 12, through series coupled 1K resistors 76, 78 to the common terminal of power supply 12, and through a 39 ohm, 2 watt resistor 80 to the anodes of LEDs 60 which are light source 22. The cathode of LEDs 60 are coupled to the common terminal of power supply 12. A meter 82 can be coupled across 1K resistor 78 and is used to check the input voltage to LEDs 60. Voltage regulator chip 66 is illustratively a LM317T manufactured by National Semiconductor, 2900 Semiconductor Drive, Santa Clara, Calif. 95051. Voltage regulator chip 66 is configured to provide a regulated +8.3 VDC to LEDs 60.

Light sensor circuit 16 includes a voltage regulator chip 84 having a V+input (pin 12) and a $V_c$ input (pin 11) coupled to the +V output of power supply 12. Voltage regulator chip 84 also has a current limit input (pin 2) coupled to a voltage output (pin 10) and a current sense input (pin 3) coupled through a 22 ohm resistor 86 to its voltage output (pin 10). An inverting input (pin 4) of voltage regulator chip 84 is coupled through series connected 47 ohm resistor 88 and 820 ohm resistor 90 and then through resistor 86 to the voltage output of voltage regulator chip 84. A non-inverting input (pin 5) of voltage regulator chip 84 is coupled through a 1K resistor 92 to a voltage reference input (pin 6) and through parallel connected 6.2K resistor 94 and 0.01 μf capacitor 96 to a V-input (pin 7) of voltage regulator chip 84. The V-input (pin 7) of voltage regulator chip 84 is also coupled to the common terminal of power supply 12 and through 100 pf capacitor 97 to a frequency compensation input (pin 13) of voltage regulator chip 84. The voltage output of voltage regulator chip 84 is coupled through resistor 86 to a first terminal of a 2.2K resistor 98 and to a first terminal of a 270K resistor 100. A second terminal of resistor 98 is coupled through a 2.2K resistor 102 to the common terminal of power supply 12. A second terminal of resistor 100 is coupled to the cathode of a photodiode 104. The anode of photodiode 104 is coupled to the common terminal of power supply 12. Photodiode 104 illustratively comprises light sensor 26. A meter 106 can be coupled across resistor 102 and be used to check the input voltage to photodiode 104. The first and second terminals of resistor 100 are coupled to inputs of analog-to-digital converter 18 and provide a voltage signal to analog-to-digital converter 18 that is indicative of the magnitude of light sensed by photodiode 104.

Photodiode 104 senses the magnitude of light reflected from the soil scene 110 and causes a voltage signal indicative thereof to be provided to the inputs of analog-to-digital converter 18. As is known, a photodiode varies the current flowing through it according to the magnitude of light it senses. The amount of current flowing through photodiode 104 is thus determined by the magnitude of light photodiode 104 senses. Since resistor 100 is in series with photodiode 104, the voltage across resistor 100 will vary according to the current flowing through photodiode 104. This voltage is provided to the input of analog-to-digital converter 18 and is the voltage signal indicative of the magnitude of light sensed by photodiode 104.

Referring to FIGS. 3-6, the operation of probe 24 is described. Arm 48, which illustratively could be a tool bar, is affixed to a vehicle such as a tractor. It is positioned so that housing 28 will be dragged through soil 108 and penetrate beneath the surface of soil 108 a predetermined distance. Illustratively, the bottom plate 34 of housing 28 will be held a set distance between three and four inches below the surface of soil 108. As has been discussed previously, the moisture content of soil affects the reflectance of the soil. At surface level, the moisture content can vary significantly. However, beneath the surface, variations in moisture content become greatly reduced. At approximately three to four inches beneath the surface, moisture content is fairly uniform in fields dry enough to permit farm vehicles such as tractors to be used.

As probe 24 is moved through the soil, housing 28 opens a soil scene 110 for observation by light sensor 26 as light source 22 and light sensor 26 are moved over the soil scene 110. As housing 28 opens the soil scene 110, flange 64 conditions the surface of soil scene 110 so that it is level and smooth. Housing 28 also encloses light source 22 and light sensor 26 and shields soil scene 110 from ambient light.

Housing 28 of probe 24 carries light source 22 and light sensor 26 over the soil scene 110 that has been opened and conditioned. Light from light source 22 is directed down onto soil scene 110 at a focal point that is illustratively one inch below the LEDs 60 that comprise light source 22 as has been discussed. As can best be seen in FIG. 3, block 54 is held in housing 28 so that LEDs 60 are one inch above soil scene 110. Light from LEDs 60 is reflected from soil scene 110 up to light sensor 26. As has been discussed, light sensor 26 causes a voltage signal to be produced at the input of analog-to-digital converter 18 that has a magnitude corresponding to the magnitude of light sensed by light sensor 26. Analog-to-digital converter 18 converts the voltage signal to a digital value corresponding to the magnitude of the voltage signal. Processor 20 processes a succession of these digital values to determine the organic matter content of soil scene 110 based upon the magnitude of light from light source 22 reflected therefrom and sensed by light sensor 26.

Figure 8:
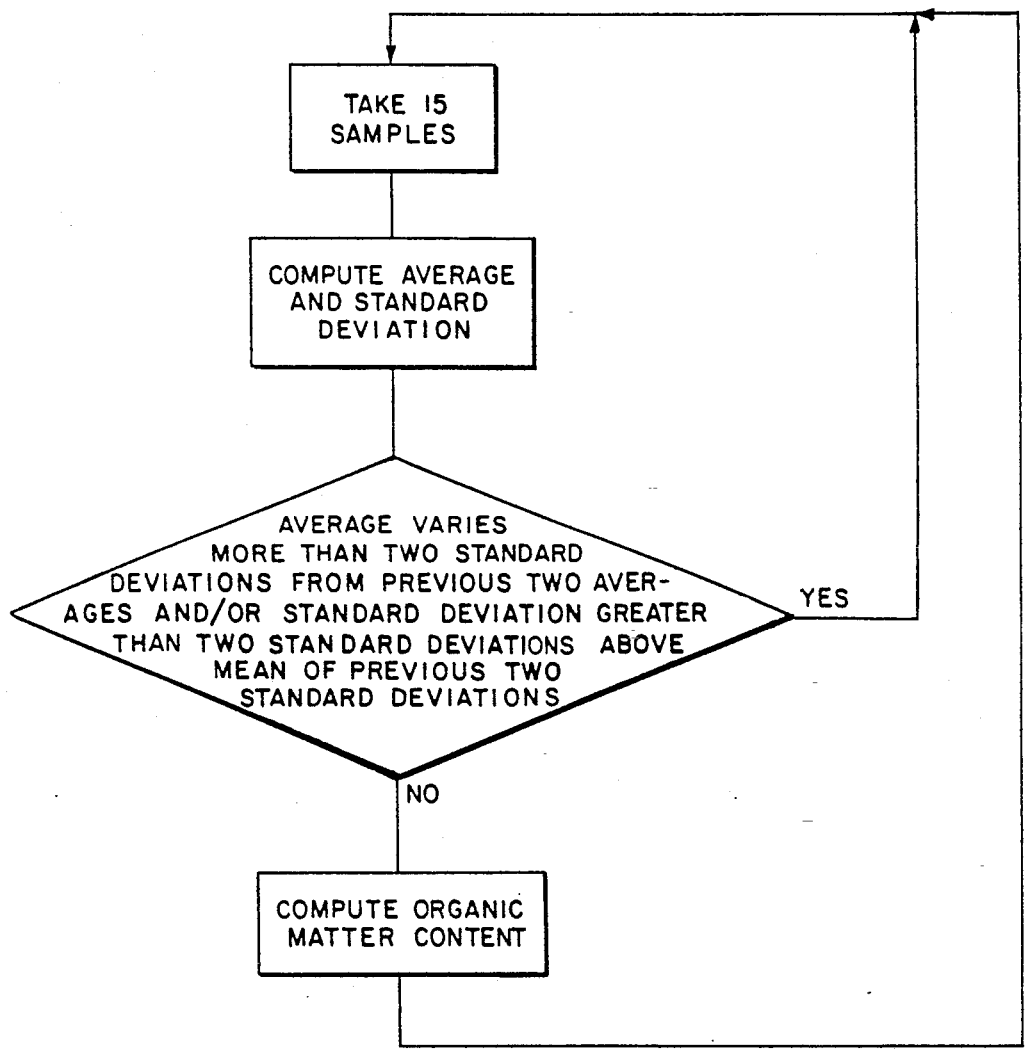
FIG. 8 is a flow chart for a program for the processor of FIG. 3.

FIG. 8 is a flow chart of an algorithm which could be used by processor 20 to determine the organic matter content of a soil scene. In the illustrative embodiment, this algorithm is executed every second. Since the vehicle to which probe 24 is attached is moving, the soil scene will actually be the small strip of soil over which probe 24 passes in a one second period. Since farm vehicles typically move fairly slow, i.e, 3-4 mph., it can be appreciated that the soil scene will be fairly small.

First, fifteen samples of reflected light readings are taken from light sensor 26. Each sample comprises the digital value of the reflected light signal produced by light sensor 26 and light sensor circuit 16 as converted by analog-to-digital converter 18. The standard deviation of these samples is then computed and the samples are also averaged. The standard deviation and average are then compared, respectively, to the average of the standard deviations of the last two sets of samples and to the average of the averages of the last two sets of samples. If the standard deviation of the current set of samples exceeds twice the standard deviation of the last two set of samples and/or the average of the current set of samples varies more than two standard deviations from the average of the previous two sets of samples, the current sample set is determined to be invalid and thrown away. This could occur if for some reason housing 28 of probe 24 comes out of the soil. The algorithm is then begun again and another set of 15 samples taken.

If the standard deviation and average of the current sample set is within limits, the organic matter content is computed using the average of the current sample set as the reflectance value. Depending upon the relative sand content of the landscape containing the soil scene 110, either equation [2] or equation [4] are used to compute the organic matter content of the soil scene 110.

Selection of the appropriate equation can be made in one of two ways. First, the landscape in question can be examined by one having knowledge of soil types, such as an agronomist, to determine whether the landscape has a relatively high or low sand content. Then, this result would be input into processor 20 to cause it to select the appropriate equation. Second, a number of soil scenes in the landscape having known organic matter contents could be examined with apparatus 10. The organic matter contents of these soil scenes would then be computed using both equations and compared to the known values which would be stored in processor 20. Based upon the results, processor 20 would determine which equation best correlated to the known values and select this equation for use. It should be understood that equations other than equations [2] and [4] could be used and would be selected for use in the same fashion. That is, the equation to be used would be selected based on the nature of the landscape where the apparatus 10 is to be used. It should also be understood that these equations are generally applicable to classes of soils that include a broad range of landscape types. For example, equation [2] is believed to be applicable for a variety of landscape types in Indiana that have relatively low sand content. Equation [4] is believed to be applicable for a variety of landscape types in Indiana having a relatively high sand content. A particular soil landscape refers to a group of soils which occur together spatially and which have formed in similar parent materials, under similar vegetation and climate, over similar periods of time. For example, soils formed in Wisconsinian aged glacial till under forest vegetation in central Indiana might comprise one soil landscape while soils formed in Wisconsinian aged glacial outwash under prairie vegetation in Northwestern Indiana might comprise another soil landscape. The parameters $B_0$ and $B_1$, on the other hand, are used to correlate the reflectance to the organic matter content for a particular type of landscape. They are experimentally determined for each type of landscape. They can be determined in the laboratory by analyzing the organic matter content from a number of locations in a specific landscape, solving the appropriate equation for $B_0$ and $B_1$, and then inputting $B_0$ and $B_1$ into processor 20. Alternatively, apparatus 10 can be used to observe a number of soil scenes having known organic matter content which is stored in processor 20. Processor 20 would then solve for $B_0$ and $B_1$ using the sampled reflectance values and known organic matter contents.

Although the invention has been described in detail with reference to certain preferred embodiments and specific examples, variations and modifications exist within the scope and spirit of the invention as described and as defined in the following claims.

What is claimed is:

1. An apparatus for attachment to a vehicle for sensing the organic matter content of soil at a soil scene, comprising:
    a probe having a housing, a light source and a light sensor;
    the housing including means for preparing the soil scene to obtain a generally uniform surface before it is observed by the light sensor;
    means for mounting the light source and the light sensor in the housing so that light from the light source is directed onto the soil scene and such that the light sensor senses light from the light source that is reflected from the soil scene; and
    means for attaching the housing to the vehicle wherein the vehicle moves the probe through the soil and the soil scene against which the light from the light source is directed is beneath the surface of the soil;
    the light sensed by the light sensor being indicative of the organic matter content of the soil scene.

2. The apparatus of claim 1 wherein the housing shields the soil scene from ambient light, the apparatus further including means for processing an output signal from the light sensor to determine the organic matter content of the soil scene and means for coupling the light sensor to the processing means.

3. The apparatus of claim 2 wherein the light sensor includes means for producing as its output signal a signal which has a magnitude indicative of the intensity of light sensed by the light sensor, the intensity of light sensed by the light sensor indicative of the magnitude of the organic matter content of the soil scene.

4. The apparatus of claim 1 wherein the means for attaching the housing to the vehicle includes an arm mounted to the vehicle having a distal end to which the housing is mounted.

5. The apparatus of claim 1 wherein the means for preparing the surface of the soil scene comprises the housing having a flange extending transversely across the housing in front of the light source and light sensor wherein the flange contacts the surface of the soil scene as it is moved across the soil scene to prepare the soil scene.

6. The apparatus of claim 5 wherein the flange has a convex lower surface that contacts the soil scene.

7. The apparatus of claim 4 wherein the housing comprises two opposed side walls, a bottom extending from front edges of the side walls part way toward rear edges of the side walls along bottom edges of the side walls, the bottom having a rear edge from which a curved flange extends transversely across the housing to contact the soil scene in front of the light sensor and light source with a convex lower surface to prepare the soil scene to have a generally uniform surface when the light from the light source is directed onto the soil, the light source and light sensor being mounted in of a rear edge of the flange.

8. The apparatus of claim 7 wherein the means for attaching the housing to the vehicle includes an arm having a distal end which is attached to the top of the housing, the housing further including a generally v-shaped front and top wall extending from a junction of the bottom and front edges of the side walls backwardly and upwardly to the arm, the housing further including a rear cover which is affixed to top edges of the side walls and extends from the arm to rear edges of the side walls.

9. The apparatus of claim 8 wherein the light sensor comprises a photodiode and the light source a plurality of red light emitting diodes arranged circularly around the photodiode.

10. The apparatus of claim 8 and further including means for processing an output signal from the light sensor to determine the organic matter content of the soil scene and means for coupling the light sensor to the processing means.

11. The apparatus of claim 10 wherein the light sensor includes means for producing as its output signal a signal which has a magnitude indicative of the intensity of light sensed by the light sensor, the intensity of light sensed by the light sensor indicative of the magnitude of the organic matter content of the soil scene.

12. The apparatus of claim 2 wherein the processing means includes a memory having data stored therein related to characteristics of the soil to be sensed including data related to the characteristics of a particular landscape which includes the soil to be sensed wherein the processing means processes the output signal from the light sensor using the stored data to determine the organic matter content of the soil scene.

13. The apparatus of claim 12 wherein the data related to characteristics of the soil to be sensed include one of a plurality of mathematical equations for a particular class of soil and the processing means processes the output signal from the light sensor by solving the mathematical equation for the class of soil being sensed for the organic matter content of the soil scene using the output signal from the light sensor as an input to the equation.

14. The apparatus of claim 13 wherein the data related to the characteristics of the soil to be sensed further includes the equation having at least one parameter related to the characteristics of said particular landscape wherein said particular landscape is within the particular class of soil.

15. An apparatus for attachment to a vehicle for sensing the organic matter content of soil at a soil scene as the vehicle moves the apparatus through the soil, the soil scene being part of a particular landscape, the soil of the landscape falling within the particular class of soil, the apparatus comprising:

a probe having a housing, a light source, a light sensor, and means for processing an output signal from the light sensor to determine the organic matter content of the soil scene;

means for mounting the light source and the light sensor in the housing so that light from the light source is directed onto the soil scene and such that the light sensor senses light from the light source that is reflected from the soil scene;

means for attaching the housing to the vehicle such that the probe is moved through the soil as the vehicle moves and the soil scene is beneath the surface of the soil;

the light sensor sensing the light from the light source that is reflected from the soil scene and producing an output signal related to the organic matter content of the soil at the soil scene;

means for coupling the light sensor to the processing means;

the processing means having an equation related to characteristics of the particular class of soil, the equation having at least one parameter related to characteristics of the soil of the particular landscape within the particular class of soil, the processing means processing the output signal from the light sensor by solving the equation for the organic matter content of the soil at the soil scene using the output signal as an input to the equation; and the housing including means for preparing the soil scene before it is observed by the light sensor to obtain a generally uniform surface.

16. A method of determining the organic matter content of soil at a soil scene comprising the steps of
directing a source of light onto the soil scene;
sensing the light reflected from the soil scene;
selecting one of a plurality of equations for a particular class of soils which includes the soil at the soil scene;
processing the sensed light to determine the organic matter content of the soil at the soil scene based upon the magnitude of the sensed light and the selected equation which correlates the magnitude of the sensed light to the organic matter content of the soil.

17. The method of claim 16 wherein the equation has at least one parameter related to characteristics of a particular landscape; and selecting said parameter for the landscape including the soil at the soil scene.

18. An apparatus for attachment to a vehicle for sensing the organic matter content of soil at a soil scene, comprising:

a probe having a housing, a light source and a light sensor;

the light sensor including a photodiode and the light source including a plurality of red light emitting diodes arranged circularly around the photodiode;

means for mounting the light source and the light sensor in the housing so that light from the light source is directed onto the soil scene and such that the light sensor senses light from the light source that is reflected from the soil scene; and means for attaching the housing to the vehicle wherein the vehicle moves the probe through the soil and the soil scene against which the light from the light source is directed is beneath the surface of the soil;

the light sensed by the light sensor being indicative of the organic matter content of the soil scene.

* * * * *